United States Patent
Anker et al.

(10) Patent No.: US 11,096,908 B2
(45) Date of Patent: Aug. 24, 2021

(54) S-ENANTIOMERICALLY ENRICHED COMPOSITIONS OF BETA BLOCKERS FOR TREATING MUSCLE WEAKNESS

(71) Applicant: ACTIMED THERAPEUTICS LTD, Ascot (GB)

(72) Inventors: Stefan Anker, Berlin (DE); Andrew J. S. Coats, Richmond (AU)

(73) Assignee: Actimed Therapeutics LTD, Ascot (GB)

( * ) Notice: Subject to any disclaimer, the term of this patent is extended or adjusted under 35 U.S.C. 154(b) by 0 days.

(21) Appl. No.: 16/078,179

(22) PCT Filed: Feb. 24, 2017

(86) PCT No.: PCT/IB2017/000267
§ 371 (c)(1),
(2) Date: Aug. 21, 2018

(87) PCT Pub. No.: WO2017/144977
PCT Pub. Date: Aug. 31, 2017

(65) Prior Publication Data
US 2019/0046476 A1    Feb. 14, 2019

Related U.S. Application Data

(60) Provisional application No. 62/300,620, filed on Feb. 26, 2016.

(51) Int. Cl.
*A61K 31/138* (2006.01)
*A61P 21/00* (2006.01)

(52) U.S. Cl.
CPC ............ *A61K 31/138* (2013.01); *A61P 21/00* (2018.01)

(58) Field of Classification Search
USPC ........................................................ 514/652
See application file for complete search history.

(56) References Cited

U.S. PATENT DOCUMENTS 2,526,959 A * 10/1950 Lorenzo ............... A61B 17/746
606/66
8,946,284 B2    2/2015 Bristow et al.

FOREIGN PATENT DOCUMENTS

| WO | 03/006001 A1 | 1/2003 |
|---|---|---|
| WO | 2010/014263 A1 | 2/2010 |
| WO | 2010/125348 A1 | 11/2010 |
| WO | WO 2014/016585 | * 1/2014 |
| WO | 2014/138806 A1 | 9/2014 |
| WO | 2014/138814 A1 | 9/2014 |

OTHER PUBLICATIONS

Graham (The effect of B-blockers on bone metabolism as potential drugs under investigation for osteoporosis and fracture healing, Expert Opinion Drugs, 2008 17(9) pp. 1281-1299).*
Levinger (Resistance training for chronic heart failure patients on beta blocker medications, International Journal of Cardiology 102 (2005) 493-499, Sep. 2004).*
Actimed (ACM-001 (S-pindolol), Feb. 2000, ACM-001 (S-pindolol)—Actimed (actimedtherapeutics.com)).*
International Search Report and Written Opinion dated Jul. 20, 2017 from International Application No. PCT/IB2017/000267 (Authorized officer, Xi Zhang), 11 pages.
R. A. Sheldon, "The Industrial Synthesis of Optically Active Compounds", Problems and Wonders of Chiral Molecules, 1990, pp. 349-386.
Agustian et al., "Single enantiomeric β-blockers—The existing technologies", Process Biochemistry, 2010, vol. 45, pp. 1587-1604.
Yashima et al., "Continuous and Preparative Enantioseparation of Oxprenolol with Cellulose Tris(3,5-dimethylphenylcarbamate)-coated Belt", Tetrahedron: Asymmetry, 1995, vol. 6, No. 8, pp. 1889-1890.
Leucuta et al., "Relative bioavailability of different oral sustained release oxprenolol tablets", Eur J Drug Metab Pharmacokinet., 1998, vol. 23, No. 2, pp. 178-184.
Bennett et al., "Single-dose pharmacokinetic and pharmacodynamic comparison of polymer-matrix (Slow Trasicor) and Oros dosage forms of oxprenolol in healthy volunteers", Br. J. Clin. Pharmac., 1985, vol. 19, Suppl 2, pp. 171S-175S.
Woods et al., "A multiple dose comparative study of the pharmacodynamic and pharmacokinetic behaviour of polymer-matrix and Oros dosage forms of oxprenolol in healthy volunteers", Br. J. Clin. Pharmac., 1985, vol. 19, Suppl 2, pp. 177S-184S.
Extended European Search Report dated Sep. 13, 2019 for European Application No. 17755893.9, 7 pages.
Stoschitzky et al., "The (R)- and (S)-enantiomers of beta-blockers are different drugs", Journal of the American College of Cardiology, Feb. 1997, vol. 29, No. 2, Suppl. A, p. 343A (Abstract).
Stoschitzky et al., "The (R)- and (S)-enantiomers of beta-blockers are different drugs", Journal of Molecular and Cellular Cardiology, Jun. 1988, vol. 30, No. 6, p. A66 (Abstract).
Coats et al., "Espindolol for the treatment and prevention of cachexia in patientswith stage III/IV non-small cell lung cancer or colorectal cancer: arandomized, double-blind, placebo-controlled, internationalmulticentre phase II study (the ACT-ONE trial)", J Cachexia Sarcopenia Muscle, 2016, vol. 7, No. 3, pp. 355-365.

* cited by examiner

*Primary Examiner* — Kathrien A Cruz
(74) *Attorney, Agent, or Firm* — MH2 Technology Law Group, LLP

(57) ABSTRACT

The use of S-enantiomerically enriched compositions of beta blockers for treating muscle weakness. The beta blocker can be oxprenolol or a pharmaceutically acceptable salt thereof.

16 Claims, No Drawings

S-ENANTIOMERICALLY ENRICHED COMPOSITIONS OF BETA BLOCKERS FOR TREATING MUSCLE WEAKNESS

CROSS-REFERENCE TO RELATED APPLICATIONS

This application is a U.S. National Stage application of PCT/IB2017/000267 filed 24 Feb. 2017, which claims priority to U.S. Provisional Patent Application No. 62/300,620 filed Feb. 26, 2016, the disclosure of which is incorporated herein by reference in its entirety.

TECHNICAL FIELD

The present invention relates to use of S-enantiomerically enriched compositions of beta blockers for treating muscle weakness. The beta blocker can be oxprenolol or a pharmaceutically acceptable salt thereof.

BACKGROUND

Skeletal muscle is a plastic tissue which readily adapts to changes in either physiological demand for work or metabolic need. Hypertrophy refers to an increase in skeletal muscle mass while skeletal muscle atrophy refers to a decrease in skeletal muscle mass. Acute skeletal muscle atrophy or muscle weakness is traceable to a variety of causes including, but not limited to: musculoskeletal injury and disuse due to surgery, immobilization, bed rest, or broken bones.

Oxprenolol is a non-selective beta blocker which possesses some intrinsic sympathomimetic activity. Because of its beta blocker function, oxprenolol has been used for the treatment of various diseases such as angina pectoris, abnormal heart rhythms, and high blood pressure. Oxprenolol is lipophilic and crosses the blood-brain barrier more easily than other more water soluble beta blockers. As a result, oxprenolol is associated with a higher incidence of CNS-related side effects than other beta blockers, but also has more central CNS modes of action.

The disclosure of all publications, patents, patent applications, and published patent applications referred to herein are hereby incorporated herein by reference in their entirety.

BRIEF SUMMARY OF THE INVENTION

The present disclosure provides, in some embodiments, a method of treating muscle weakness in an individual, comprising administering to the individual an effective amount of an S-enantiomerically enriched composition of a beta blocker or a pharmaceutically acceptable salt thereof.

The present disclosure provides, in some embodiments, a method of preventing body weight loss in an individual with muscle weakness, comprising administering to the individual an effective amount of an S-enantiomerically enriched composition of a beta blocker or a pharmaceutically acceptable salt thereof.

The present disclosure provides, in some embodiments, a method of preventing and treating muscle wasting in an individual with muscle weakness, comprising administering to the individual an effective amount of an S-enantiomerically enriched composition of a beta blocker or a pharmaceutically acceptable salt thereof.

The present disclosure provides, in some embodiments, a method of improving quality of life in an individual with muscle weakness, comprising administering to the individual an effective amount of an S-enantiomerically enriched composition of a beta blocker or a pharmaceutically acceptable salt thereof.

In some embodiments, the beta blocker is oxprenolol or a pharmaceutically acceptable salt thereof.

In some embodiments, the muscle weakness is in an acute state. In some embodiments, the muscle weakness is localized. In some embodiments, wherein the individual has suffered a musculoskeletal injury. In some embodiments, the individual has undergone surgery. In some embodiments, the surgery is abdominal, orthopedic, cardiac, brain, lung, eye, or head and neck. In some embodiments, the individual has been immobilized. In some embodiments, the individual has been immobilized for at least 48 hours. In some embodiments, the individual has suffered a major trauma. In some embodiments, the trauma affects large bones, abdominal organs, chest organs, or head.

In some embodiments, the composition comprises an enantiomeric excess of at least about 50% of an S-enantiomerically enriched composition of a beta blocker or a pharmaceutically acceptable salt thereof. In some embodiments, the composition comprises an enantiomeric excess of at least about 80% of an S-enantiomerically enriched composition of a beta blocker or a pharmaceutically acceptable salt thereof. In some embodiments, the composition comprises an enantiomeric excess of at least about 99% of an S-enantiomerically enriched composition of a beta blocker or a pharmaceutically acceptable salt thereof. In some embodiments, the composition comprises an enantiomeric excess of at least about 99.9% of an S-enantiomerically enriched composition of a beta blocker or a pharmaceutically acceptable salt thereof.

In some embodiments, the composition comprises an enantiomeric excess of at least about 50% of S-oxprenolol or a pharmaceutically acceptable salt thereof. In some embodiments, the composition comprises an enantiomeric excess of at least about 80% of S-oxprenolol or a pharmaceutically acceptable salt thereof. In sonic embodiments, the composition comprises an enantiomeric excess of at least about 99% of S-oxprenolol or a pharmaceutically acceptable salt thereof. In some embodiments, the composition comprises an enantiomeric excess of at least about 99.9% of S-oxprenolol or a pharmaceutically acceptable salt thereof. In some embodiments, the composition is administered orally. In some embodiments, the amount of S-oxprenolol or a pharmaceutically acceptable salt thereof in the composition is about 80 to about 160 mg daily. In some embodiments, the composition is administered daily or twice daily.

The present disclosure provides, in some embodiments, a pharmaceutical composition comprising a beta blocker or a pharmaceutically acceptable salt thereof and a pharmaceutically acceptable carrier for use in treating muscle weakness. In some embodiments, the beta blocker is oxprenolol or a pharmaceutically acceptable salt thereof.

The present disclosure provides, in some embodiments, a kit comprising a pharmaceutical composition comprising a beta blocker or a pharmaceutically acceptable salt thereof and a pharmaceutically acceptable carrier and instruction for using the pharmaceutical composition for treating muscle weakness. In some embodiments, the beta blocker is oxprenolol or a pharmaceutically acceptable salt thereof.

DETAILED DESCRIPTION OF THE INVENTION

The present invention provides use of an S-enantiomerically enriched composition of a beta blocker for achieving beneficial results in individuals having muscle weakness. In an S-enantiomerically enriched composition of a beta blocker or a pharmaceutically acceptable salt thereof, the beta blocker or a pharmaceutically acceptable salt thereof has one chiral center and the composition is enantiomerically enriched for the S-enantiomer. Thus, as used herein, "S-enantiomerically enriched composition of a beta blocker" refers to a beta blocker having one chiral center and the composition is enantiomerically enriched for the S-enantiomer. In some embodiments, the beta blocker is oxprenolol or a pharmaceutically acceptable salt thereof.

Thus, the present invention, in one aspect, provides methods of treating muscle weakness in an individual, comprising administering to the individual an effective amount of an S-enantiomerically enriched composition of a beta blocker or a pharmaceutically acceptable salt thereof. In some embodiments, the muscle weakness is an acute state in the individual. In some embodiments, the muscle weakness is localized in the individual. In some embodiments, the beta blocker is oxprenolol or a pharmaceutically acceptable salt thereof.

Also provided are kits, unit dosages, medicines, and articles of manufacture that are useful for methods described herein.

Definitions

The following terms have the following meanings unless otherwise indicated. Any undefined terms have their art recognized meanings.

As used herein, "treatment" or "treating" is an approach for obtaining beneficial or desired results including clinical results. For purposes of this invention, beneficial or desired clinical results include, but are not limited to, one or more of the following: alleviating one or more symptoms resulting from the condition, diminishing the extent of the condition, stabilizing the condition preventing or delaying the worsening of the condition), preventing or delaying the spread of the condition, preventing or delaying the recurrence of the condition, delay or slowing the progression of the condition, ameliorating the condition state, providing a remission (partial or total) of the condition, decreasing the dose of one or more other medications required to treat the condition, delaying the progression of the condition, increasing the quality of life, and/or prolonging survival. Also encompassed by "treatment" is a reduction of pathological consequence of muscle weakness. The methods of the invention contemplate any one or more of these aspects of treatment.

The term "individual" refers to a mammal and includes, but is not limited to, human, bovine, horse, feline, canine, rodent, or primate. In some embodiments, the individual is a human.

As used herein, an "at risk" individual is an individual who is at risk of developing muscle weakness. An individual "at risk" may or may not have detectable condition, and may or may not have displayed detectable condition prior to the treatment methods described herein. "At risk" denotes that an individual has one or more so-called risk factors, which are measurable parameters that correlate with development of muscle weakness. An individual having one or more of these risk factors has a higher probability of developing muscle weakness than an individual without these risk factor(s).

As used herein, "delaying" the development of a condition means to defer, hinder, slow, retard, stabilize, and/or postpone development of the condition. This delay can be of varying lengths of time, depending on the history of the condition and/or individual being treated. As is evident to one skilled in the art, a sufficient or significant delay can, in effect, encompass prevention, in that the individual does not develop the condition. A method that "delays" development of a condition is a method that reduces probability of condition development in a given time frame and/or reduces the extent of the condition in a given time frame, when compared to not using the method. Such comparisons are typically based on clinical studies, using a statistically significant number of subjects.

As used herein, by "combination therapy" is meant that a first agent be administered in conjunction with another agent. "In conjunction with" refers to administration of one treatment modality in addition to another treatment modality, such as administration of a composition described herein in addition to administration of the other agent to the same individual. As such, "in conjunction with" refers to administration of one treatment modality before, during, or after delivery of the other treatment modality to the individual. Such combinations are considered to be part of a single treatment regimen or regime.

The term "effective amount" used herein refers to an amount of a compound or composition sufficient to treat a specified disorder, condition or disease such as ameliorate, palliate, lessen, and/or delay one or more of its symptoms. In reference to muscle weakness, an effective amount comprises an amount sufficient to prevent or delay unwanted symptoms associated with muscle weakness. In some embodiments, an effective amount is an amount sufficient to delay development. In some embodiments, an effective amount is an amount sufficient to prevent or delay recurrence. An effective amount can be administered in one or more administrations.

The term "simultaneous administration," as used herein, means that a first therapy and second therapy in a combination therapy are administered with a time separation of no more than about 15 minutes, such as no more than about any of 10, 5, or 1 minutes. When the first and second therapies are administered simultaneously, the first and second therapies may be contained in the same composition (e.g., a composition comprising both a first and second therapy) or in separate compositions e.g., a first therapy in one composition and a second therapy is contained in another composition).

As used herein, the term "sequential administration" means that the first therapy and second therapy in a combination therapy are administered with a time separation of more than about 15 minutes, such as more than about any of 20, 30, 40, 50, 60, or more minutes. Either the first therapy or the second therapy may be administered first. The first and second therapies are contained in separate compositions, which may be contained in the same or different packages or kits.

As used herein, the term "concurrent administration" means that the administration of the first therapy and that of a second therapy in a combination therapy overlap with each other.

As used herein, by "pharmaceutically acceptable" or "pharmacologically compatible" is meant a material that is not biologically or otherwise undesirable, e.g., the material may be incorporated into a pharmaceutical composition administered to an individual without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

An "adverse event" or "AE" as used herein refers to any untoward medical occurrence in an individual receiving a marketed pharmaceutical product or in an individual who is participating on a clinical trial who is receiving an investigational or non-investigational pharmaceutical agent.

The term "isomers" or "stereoisomers" refers to compounds which have identical chemical constitution, but differ with regard to the arrangement of the atoms or groups in space.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not mirror images of one another.

The term "enantiomers" refers to two stereoisomers of a compound which are non-superimposable mirror images of one another. An equimolar mixture of two enantiomers is called a "racemic mixture" or a "racemate."

The term "enantiomerically enriched" means that the racemic mixture (i.e., 50/50 mixture of the enantiomers) has been purified such that one enantiomer comprises greater than 50% of the total amount of the compound present. For example, a composition that is enantiomerically enriched for S-oxprenolol is a composition wherein more than 50% of the oxprenolol is the S-enantiomer of oxprenolol (S-oxprenolol).

The degree of enantiomeric enrichment of a composition can be determined by "enantiomeric excess," or ee. "Enantiomeric excess" represents the percentage of one enantiomer in excess of the other. For instance, a composition having a 75:25 mixture of S-oxprenolol and R-oxprenolol has a 75-25 =50% ee, while a 50:50 racemic mixture has a 50−50=0% ee. The value of ee will be a number from 0 to 100, 0 being racemic and 100 being pure, single enantiomer.

The term "pharmaceutically acceptable salt" means a salt which is acceptable for administration to a subject, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to the subject. By way of example, salts of the present compounds include those wherein the compound is protonated by an inorganic or organic acid to form a cation, with the conjugate base of the inorganic or organic acid as the anionic component of the salt.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

It will be appreciated that the term "or a salt or solvate thereof" is intended to include all permutations of salts and solvates, such as a solvate of a pharmaceutically acceptable salt of a subject compound.

As used herein, "in conjunction with" refers to administration of one treatment modality in addition to another treatment modality. As such, "in conjunction with" refers to administration of one treatment modality before, during or after administration of the other treatment modality to the individual.

As used herein and in the appended claims, the singular forms "a," "an," and "the" include plural reference unless the context clearly indicates otherwise.

Reference to "about" a value or parameter herein includes (and describes) embodiments that are directed to that value or parameter per se. For example, description referring to "about X" includes description of "X."

It is understood that aspects and variations of the invention described herein include "consisting" and/or "consisting essentially of" aspects and variations.

Methods of the Present Invention

The present invention provides use of an S-enantiomerically enriched composition of a beta blocker for achieving beneficial results in individuals having muscle weakness.

In some embodiments, there is provided a method of treating muscle weakness in an individual, comprising administering to the individual an effective amount of an S-enantiomerically enriched composition of a beta blocker or a pharmaceutically acceptable salt thereof (such as a composition having at least about any one of 10%, 20%, 30%, 40%, 50%, 60%, 70%, 80%, 90%, 95%, 96%, 97%, 98%, 99%, or 99.9% ee). In some embodiments, the beta blocker is selected from the group consisting of acebutolol, atenolol, betaxolol, bisoprolol, carteolol, celeprolol, labetalol, metoprolol, nadolol, nehivolol, oxprenolol, penbutolol, propanolol, sotalol, esmolol, carvedilol, timolol, bopindolol, medroxalol, bucindolol, levobunolol, metipranolol, celiprolol and propafenone. In some embodiments, the beta blocker is oxprenolol or a pharmaceutically acceptable salt thereof. In some embodiments, the composition comprises an enantiomeric excess of at least about 10% (such as at least about any one of 20%, 30%, 40%, 50%, 60%, 70%, 80%, 90%, 95%, 96%, 97%, 98%, 99%, or 99.9%) of S-oxprenolol. In some embodiments, there is provided a method of treating muscle weakness in an individual, comprising administering to the individual an effective amount of a composition comprising oxprenolol or a pharmaceutically acceptable salt thereof, wherein the composition comprises an enantiomeric excess of at least about 99% (for example at least about 99.9%) of S-oxprenolol. In some embodiments, there is provided a method of treating muscle weakness in an individual, comprising administering (such as orally administering) to the individual an effective amount of a composition comprising oxprenolol or a pharmaceutically acceptable salt thereof, wherein the composition is enantiomerically enriched for S-oxprenolol (for example comprises an enantiomeric excess of at least about 99% of S-oxprenolol). In some embodiments, the amount of S-oxprenolol in the composition is about 50 mg to about 160 mg (such as about 80 to about 160 mg, for example about 100 mg to about 160 mg).

Muscle weakness refers to a reduction in the strength of one or more muscles. To assess muscle weakness, there are several tests available. In some embodiments, muscle weakness can be assessed by short physical performance battery scores and standard clinical assessment of functional performance, muscle strength, gait speed, leg strength and hand grip strength, 6-minute corridor walk test, and stair climbing power. In some embodiments, muscle weakness can he assessed by simple bedside testing such as asking the patient to perform a handgrip, arm bend, arm raise, leg raise, foot dorsiflexion or similar limb or body movements against resistance and assess whether the strength is perceived by either or both of the doctor or patient as weaker than would be expected.

Treatment of muscle weakness can be assessed by improvement of muscle strength over time based on the available tests. In some embodiments, an improvement of about 1,2, 3, 4, 5, 6, 7, 8, 9, 10% or more based on any of the tests disclosed herein over 1, 2, 3, 4, 5, 6, or 7 days indicates treatment of muscle weakness. Any subjective report by the patient that strength has improved, or any objective test improvement by at least 1, 2, 3, 4, 5, 6, 7, 8, 9, 10% or more would be proof of effective treatment.

In some embodiments, the muscle weakness is in an acute state in an individual. For an acute state, the muscle weakness would have been occurring for a short duration. In an acute state, muscle weakness would have been lasting up to 1, 2, 3, or 4 weeks. In some embodiments, acute muscle weakness would have been lasting up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days. The muscle weakness would be acute as evidenced by any of the patient, a relative or friend reporting that the muscle weakness has occurred or worsened in the last 1, 2, 3, or 4 weeks.

In some embodiments, the muscle weakness is localized in an individual. By localized, muscle weakness is confined to one area of the body in an individual. In some embodiments, localized muscle weakness can occur at a limb (e.g. arm, hand, leg, or foot), neck, back, chest, or head.

In some embodiments, the muscle weakness produces secondary effects, such as body weight loss, lowering the quality of life, and muscle wasting.

In some embodiments, there is provided a method of preventing body weight loss of an individual with muscle weakness, comprising administering to the individual an effective amount of an S-enantiomerically enriched composition of a beta blocker or a pharmaceutically acceptable salt thereof (such as a composition having at least about any one of 10%, 20%, 30%, 40%, 50%, 60%, 70%, 80%, 90%, 95%, 96%, 97%, 98%, 99%, or 99.9% ee). In some embodiments, the beta blocker is selected from the group consisting of acebutolol, atenolol, betaxolol, bisoprolol, carteolol, celeprolol, labetalol, metoprolol, nadolol, nebivolol, oxprenolol, penbutolol, pindolol, propanolol, sotalol, esmolol, carvedilol, timolol, bopindolol, medroxalol, bucindolol, levobunolol, metipranolol, celiprolol and propafenone. In some embodiments, the beta blocker is oxprenolol or a pharmaceutically acceptable salt thereof. In some embodiments, the composition comprises an enantiomeric excess of at least about 10% (such as at least about any one of 20%, 30%, 40%, 50%, 60%, 70%, 80%, 90%, 95%, 96%, 97%, 98%, 99%, or 99.9%) of S-oxprenolol. In some embodiments, there is provided a method of preventing body weight loss in an individual with muscle weakness, comprising administering to the individual an effective amount of a composition comprising oxprenolol or a pharmaceutically acceptable salt thereof, wherein the composition comprises an enantiomeric excess of at least about 99% (for example at least about 99.9%) of S-oxprenolol. In some embodiments, there is provided a method of preventing body weight loss of an individual with muscle weakness, comprising administering (such as orally administering) to the individual an effective amount of a composition comprising oxprenolol or a pharmaceutically acceptable salt thereof, wherein the composition is enantiomerically enriched for S-oxprenolol (for example comprises an enantiomeric excess of at least about 99% of S-oxprenolol). In some embodiments, the amount of S-oxprenolol in the composition is about 50 mg to about 160 mg (such as about 80 to about 160 mg, for example about 100 mg to about 160 mg). In some embodiments, the body weight loss of the individual is no more than about 20% (for example no more than about any of 15%, 14%, 13%, 12%, 11%, 10%, 9%, 8%, 7%, 6%, or 5%) of the total body weight. In some embodiments, the body weight loss is evaluated over a time period of about 1 day to 1 month (for example, about 1, 2, 3, 4, 5, 6, 7, 8, 9, 10, 11, 1:2, 13, 14, 15, 16, 17, 18, 19, 20, 21, 24, 25, 26, 27, 28, 29, or 30 days). In some embodiments, the body weight loss is evaluated over a time period of about 1 month to 2 years (for example, about 1, 2, 3, 4, 5, 6, 7, 8, 9, 10, 11, 12, 13, 14, 15, 16, 17, 18, 19, 20, 21, 22, 23, or 24 months).

In some embodiments, there is provided a method of treating muscle wasting in an individual with muscle weakness, comprising administering to the individual an effective amount of an S-enantiomerically enriched composition of a beta blocker or a pharmaceutically acceptable salt thereof (such as a composition having at least about any one of 10%, 20%, 30%, 40%, 50%, 60%, 70%, 80%, 90%, 95%, 96%, 97%, 98%, 99%, or 99.9% ee). In some embodiments, the beta blocker is selected from the group consisting of acebutolol, atenolol, betaxolol, bisoprolol, carteolol, celeprolol, labetalol, metoprolol, nadolol, nebivolol, oxprenolol, penbutolol, pindolol, propanolol, sotalol, esmolol, carvedilol, timolol, bopindolol, medroxalol, bucindolol, levobunolol, metipranolol, celiprolol and propafenone. In some embodiments, the beta blocker is oxprenolol or a pharmaceutically acceptable salt thereof. In some embodiments, the composition comprises an enantiomeric excess of at least about 10% (such as at least about any one of 20%, 30%, 40%, 50%, 60%, 70%, 80%, 90%, 95%, 96%, 97%, 98%, 99%, or 99.9%) of S-oxprenolol. In some embodiments, there is provided a method of treating muscle wasting in an individual with muscle weakness, comprising administering to the individual an effective amount of a composition comprising oxprenolol or a pharmaceutically acceptable salt thereof, wherein the composition comprises an enantiomeric excess of at least about 99% (for example at least about 99.9%) of S-oxprenolol. In some embodiments, there is provided a method of treating muscle wasting in an individual with muscle weakness, comprising administering such as orally administering) to the individual an effective amount of a composition comprising oxprenolol or a pharmaceutically acceptable salt thereof, wherein the composition is enantiomerically enriched for S-oxprenolol (for example comprises an enantiomeric excess of at least about 99% of S-oxprenolol). In some embodiments, the amount of S-oxprenolol in the composition is about 50 mg to about 160 mg (such as about 80 to about 160 mg, for example about 100 mg to about 160 mg). In some embodiments, the muscle wasting of the individual is no more than about 10% (for example no more than about any of 10%, 9%, 8%, 7%, 6%, or 5%) of the total body weight. In some embodiments, the muscle wasting is evaluated over a time period of about 1 day to 1 month (for example, about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days). In some embodiments, the muscle wasting is evaluated over a time period of about 1 month to 2 years (for example, about 1, 2, 3, 4, 5, 6, 7, 8, 9, 10, 11, 12, 13, 14, 15, 16, 17, 18, 19, 20, 21, 22, 23, or 24 months). In some embodiments, the method leads to a reduction of muscle wasting, i.e., a slow-down of muscle loss in the individual. In some embodiments, the method leads to a reversal of muscle wasting, i.e., an increase in muscle weight in the individual.

In some embodiments, there is provided a method of improving quality of life of an individual with muscle weakness, comprising administering to the individual an effective amount of an S-enantiomerically enriched composition of a beta blocker or a pharmaceutically acceptable salt thereof (such as a composition having at least about any one of 10%, 20%, 30%, 40%, 50%, 60%, 70%, 80%, 90%, 95%, 96%, 97%, 98%, 99%, or 99.9% ee). In some embodiments, the beta blocker is selected from the group consisting of acebutolol, atenolol, betaxolol, bisoprolol, carteolol, celeprolol, labetalol, metoprolol, nadolol, nebivolol, oxprenolol, penbutolol, pindolol, propanolol, sotalol, esmolol, carvedilol, timolol, bopindolol, medroxalol, bucindolol, levobunolol, metipranolol, celiprolol and propafenone. In some embodiments, the beta blocker is oxprenolol or a pharmaceutically acceptable salt thereof. In some embodiments, the composition comprises an enantiomeric excess of at least about 10% (such as at least about any one of 20%, 30%, 40%, 50%, 60%, 70%, 80%, 90%, 95%, 96%, 97%, 98%, 99%, or 99.9%) of S-oxprenolol. In some embodiments, there is provided a method of improving quality of life of an individual with muscle weakness, comprising administering to the individual an effective amount of a composition comprising oxprenolol or a pharmaceutically acceptable salt thereof, wherein the composition comprises an enantiomeric excess of at least about 99% (for example at least about 99.9%) of S-oxprenolol. In some embodiments, there is provided a method of improving quality of life of an individual with muscle weakness, comprising administering (such as orally administering) to the individual an effective amount of a composition comprising oxprenolol or a pharmaceutically acceptable salt thereof, wherein the composition is enantiomerically enriched for S-oxprenolol (for example comprises an enantiomeric excess of at least about 99% of S-oxprenolol). In some embodiments, the amount of S-oxprenolol in the composition is about 50 mg to about 160 mg (such as about 80 to about 160 mg, for example about 100 mg to about 160 mg). Improvement of quality of life can be assessed, for example, by food intake, locomotive activity, improvement in fatigue or dyspnea or global patient assessment scores, in short physical performance battery scores, in standard clinical assessment of functional performance, muscle strength, gait speed, leg strength and hand grip strength, 6-minute corridor walk test, stair climbing power, ability to tolerate courses of chemotherapy and other tests or instruments or questionnaires assessing patient quality of life.

In some embodiments, the individual has suffered a musculoskeletal injury. In some embodiments, musculoskeletal injury includes fractures, joint dislocations, ligament sprains, muscle strains, and tendon injuries. In some embodiments, musculoskeletal injury includes Carpal Tunnel Syndrome, tendonitis, muscle/tendon strain, ligament sprain, tension neck syndrome, thoracic outlet compression, rotator cuff tendonitis, epicondylitis, radial tunnel syndrome, digital neuritis, trigger finger/thumb, DeQuervain's Syndrome, mechanical back syndrome, degenerative disc disease, and ruptured/herniated disc. In some embodiments, the musculoskeletal injury results in immobilization of the individual.

In some embodiments, the individual has undergone surgery. In some embodiments, the surgery is abdominal, orthopedic, cardiac, brain, lung, eye, or head and neck. In some embodiments, the surgery results in immobilization of the individual.

In some embodiments, the individual has been immobilized. In some embodiments, the individual has been immobilized for at least 12, 24, 48, 60, or 72 hours. In some embodiments, the individual has been immobilized for at least 1, 2, 3, 4, 5, 6, or 7 days.

In some embodiments, the immobilization is a result of major trauma, bone fracture, sprains, dislocations, muscle tears, disruptions or crush injuries, or an acute disabling illness, including myocardial infarction, stroke, and neurological disorder, such as Guillain-Barre syndrome. In some embodiments, the immobilization is a result of enforced bed rest.

In some embodiments, the individual has suffered a major trauma. As used herein, "trauma" is a body wound or shock produced by sudden physical injury as from violence or accident or a physical wound or injury, such as a fracture, blow, or surgical procedure, which results in major muscle tissue damage. In some embodiments, the major trauma affects large bones, abdominal organs, chest organs, or head.

In some embodiments, the individual has suffered fractures of the long bones of the arm or leg. In some embodiments, the individual has suffered a ligament sprain or muscle strain. In some embodiments, the individual has suffered a tendon injury. In some embodiments, the individual has suffered a joint dislocation.

In some embodiments, muscle weakness is associated with denervation/nerve damage due to spinal cord injury, autoimmune disease, or infectious disease; glucocorticoid use for unrelated conditions; sepsis due to infection or other causes; nutrient limitation due to illness or starvation; or space travel.

Beta Blockers

The methods described herein comprise administration of compositions comprising beta blockers. Beta blockers, which are used to treat hypertension, can be used for treating muscle weakness.

In some embodiments, where the beta blocker contains one chiral center, the beta blocker is the enantiomerically enriched S-enantiomer or a pharmaceutically acceptable salt thereof.

In some embodiments, the beta blocker is selected from the group consisting of acebutolol, atenolol, betaxolol, bisoprolol, carteolol, celeprolol, labetalol, metoprolol, nadolol, nebivolol, oxprenolol, penbutolol, pindolol, propanolol, sotalol, esmolol, carvedilol, timolol, bopindolol, medroxalol, bucindolol, levobunolol, metipranolol, celiprolol and propafenone. In some embodiments, the beta blocker is oxprenolol. Oxprenolol is a non-selective beta blocker which possesses some intrinsic sympathomimetic activity.

In some embodiments, the beta blocker also has partial 5-$HT_{1A}$ agonism activity. The 5-$HT_{1A}$ receptor is a subtype of 5-HT receptor that binds the endogenous neurotransmitter serotonin (5-hydroxytryptamine, 5-HT). Oxprenolol is a partial 5-HT1a agonist.

S-Enantiomerically Enriched Compositions of Beta Blockers

The methods described herein comprise administration of an S-enantiomerically enriched composition of a beta blocker or a pharmaceutically acceptable salt thereof (for example comprising an enantiomeric excess of at least about 99% of a beta blocker).

When a compound has a chiral center, the compound can exist in optically active forms. Optically active compounds have the ability to rotate the plane of plane-polarized light. In describing an optically active compound, the prefixes R and S are used to denote the absolute configuration of the molecule about its chiral center(s). The prefixes "d" and "l" or (+) and (−) are employed to designate the sign of rotation of plane-polarized light by the compound, with (−) or l meaning that the compound is "levorotatory" and with (+) or d meaning that the compound is "dextrorotatory." There is no correlation between nomenclature for the absolute stereochemistry and for the rotation of an enantiomer. For a given chemical structure, these compounds, called "stereoisomers," are identical except that they are mirror images of one another. A specific stereoisomer can also be referred to as an "enantiomer," and a mixture of such isomers is often called an "enantiomeric" or "racemic" mixture. When a compound has one chiral center, there are two enantiomers: the S-enantiomer and the R-enantiomer.

The compositions useful for treating muscle weakness described herein are enantiomerically enriched for S-enantiomer. For example, in some embodiments, the composition useful for treating muscle weakness comprises an enantiomeric excess of at least about 1%, 5%, 10%, 15%, 20%, 25%, 30%, 35%, 40%, 45%, 50%, 55%, 60%, 65%, 70%, 75%, 80%, 85%, 90% or 95% of S-enantiomer of the beta blocker. In some embodiments, the composition useful for treating muscle weakness comprises an enantiomeric excess of at least about 90%, 91%, 92%, 93%, 94%, 95%, 96%, 97%, 98%, 99%, or 99.9% of S-enantiomer of the beta blocker. In some embodiments, the composition useful for treating muscle weakness comprises an enantiomeric excess of at least about 90%, 95%, 98%, 99%, or 100%, up to the detectable limit of purity, of S-enantiomer of the beta blocker. In some embodiments, the composition useful for treating muscle weakness comprises an enantiomeric excess of any of about 1-4%, 5-9%, 10-19%, 20-29%, 30-39%, 40-49%, 50-59%, 60-69%, 70-79%, 80-89%, 90-99%, or 100% of S-enantiomer of the beta blocker. In some embodiments, the composition useful for treating muscle weakness comprises an enantiomeric excess of at least about 99% or 100% of S-enantiomer of the beta blocker (i.e., pure S-enantiomer of the beta blocker). In some embodiments, the composition useful for treating muscle weakness comprises an enantiomeric excess of at least 99.1, 99.2, 99.3, 99.4, 99.5, 99.6, 99.7, 99.8, 99.9 or 100% of S-enantiomer of the beta blocker (i.e., pure S-enantiomer of the beta blocker). Methods of making enantiomerically enriched compositions of beta blockers are known in the art.

In some embodiments, the beta blocker is selected from the group consisting of acebutolol, atenolol, betaxolol, bisoprolol, carteolol, celeprolol, labetalol, metoprolol, nadolol, nebivolol, oxprenolol, penbutolol, pindolol, propanolol, sotalol, esmolol, carvedilol, timolol, bopindolol, medroxalol, bucindolol, levobunolol, metipranolol, celiprolol and propafenone or a pharmaceutically acceptable salt thereof.

In some embodiments, the beta blocker oxprenolol or a pharmaceutically acceptable salt thereof. Oxprenolol is 1-[2-(allyloxy)phenoxy]-3-(isopropylamino)propan-2-ol. The structure of oxprenolol is shown below.

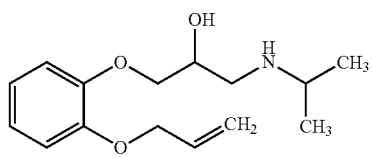 [SMILES: C=CCOc1ccccc1OCC(O)CNC(C)C]

Oxprenolol is a compound with one chiral center. As a racemic mixture, there is a mixture of (R)-(+)-oxprenolol and (S)-(−)-oxprenolol. Analytical methods, such as HPLC, can be used for separation and quantification of (R)-(+)-oxprenolol and (S)-(−)-oxprenolol in mixtures. The structures of (R)-(+)-oxprenolol and (S)-(−)-oxprenolol are shown below.

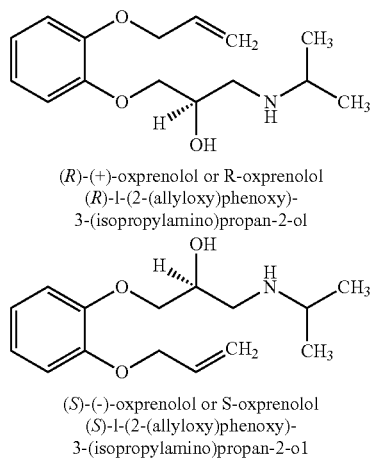

(R)-(+)-oxprenolol or R-oxprenolol
(R)-1-(2-(allyloxy)phenoxy)-
3-(isopropylamino)propan-2-ol (S)-(−)-oxprenolol or S-oxprenolol
(S)-1-(2-(allyloxy)phenoxy)-
3-(isopropylamino)propan-2-ol The compositions useful for treating muscle weakness described herein are enantiomerically enriched for S-oxprenolol. For example, in some embodiments, the composition useful for treating muscle weakness comprises an enantiomeric excess of at least about 1%, 5%, 10%, 15%, 20%, 25%, 30%, 35%, 40%, 45%, 50%, 55%, 60%, 65%, 70%, 75%, 80%. 85%, 90% or 95% of S-oxprenolol. In some embodiments, the composition useful for treating muscle weakness comprises an enantiomeric excess of at least about 90%, 91%, 92%, 93%, 94%, 95%, 96%, 97%, 98%, 99%, or 99.9% of S-oxprenolol. In some embodiments, the composition useful for treating muscle weakness comprises an enantiomeric excess of at least about 90%, 95%, 98%, 99%, or 100%, up to the detectable limit of purity, of S-oxprenolol. In some embodiments, the composition useful for treating muscle weakness comprises an enantiomeric excess of any of about 1-4%, 5-9%, 10-19%, 20-29%, 30-39%, 40-49%, 50-59%, 60-69%, 70-79%, 80-89%, 90-99%, or 100% of S-oxprenolol. In some embodiments, the composition useful for treating muscle weakness comprises an enantiomeric excess of at least about 99% or 100% of S-oxprenolol (i.e., pure S-oxprenolol). In some embodiments, the composition useful for treating muscle weakness comprises an enantiomeric excess of at least 99.1, 99.2, 99.3, 99.4, 99.5, 99.6, 99.7, 99.8, 99.9 or 100% of S-oxprenolol (i.e., pure S-oxprenolol). Methods of making enantiomerically enriched compositions of oxprenolol are known in the art.

Two main routes are established for obtaining enantiomerically enriched compounds: (1) asymmetric syntheses and (2) racemic resolutions. (R. A. Sheldon: *The Industrial Synthesis of Optically Active Compounds*, in Miklós Simonyi (editor), *Problems and Wonders if Chiral Molecules*, Akadémiai Kiadó, Budapest, 1990, S. 349-386). The syntheses give medium-high yields and excellent enantiomeric excess, but the resolutions are limited by 50% yield. Both technologies involve techniques such as dynamic kinetic resolution (DKR) and membrane-based extraction (Augustian J et al., Process Biochemistry Volume 45, Issue 10, October 2010, Pages 1587-1604). One method describes enantiomer enrichment of oxprenolol up to 68% enantiomeric excess was achieved by using a cellulose tris(3,5-dimethylphenylcarbamate) (CTPC)-coated rayon-belt. (Yashima E. et al., Tetrahedron: Asymmetry Volume 6, Issue 8, August 1995, Pages 1889-1890).

The compositions useful for treating muscle weakness described herein in some embodiments are present in pharmaceutical compositions. The pharmaceutical compositions may further comprise one or more pharmaceutically acceptable carrier (or excipients). A pharmaceutically-acceptable excipient is a substance that is non-toxic and otherwise biologically suitable for administration to a subject. Such excipients facilitate administration of the compounds described herein and are compatible with the active ingredient. Examples of pharmaceutically-acceptable excipients include stabilizers, lubricants, surfactants, diluents, antioxidants, binders, coloring agents, bulking agents, emulsifiers, or taste-modifying agents. In some embodiments, the pharmaceutical composition is sterile.

Also provided here are unit dosage forms comprising a pharmaceutical compositions useful for treating muscle weakness described herein. These unit dosage forms can be stored in a suitable packaging in single or multiple unit dosages and may also be further sterilized and sealed. Unit dosage forms can he provided, for example, in the form of tablets, capsules, vials, and any other forms described herein.

In some embodiments, there is provided a composition (such as a pharmaceutical composition, for example a unit dosage) useful for treating muscle weakness comprising oxprenolol or a pharmaceutically acceptable salt thereof, wherein the composition is enantiomerically enriched for S-oxprenolol (for example comprising an enantiomeric excess of at least about 99% of S-oxprenolol), wherein the amount of S-oxprenolol in the composition (such as pharmaceutical composition) is included in any of the following ranges: about 5 to about 10 mg, about 10 to about 20 mg, about 20 to about 30 mg, about 30 to about 40 mg, about 40 to about 50 mg, about 50 to about 60 mg, about 60 to about 70 mg, about 70 to about 80 mg, about 80 to about 90 mg, about 90 to about 100 mg, about 100 to about 110 mg, about 110 to about 120 mg, about 120 to about 130 mg, about 130 to about 140 mg, about 140 to about 150 mg, about 150 to about 160 mg. In some embodiments, the amount of S-oxprenolol in the composition is about 20 to about 160 mg, including for example about 50 to about 150 mg, 80 to about 150 mg, about 90 to about 140 mg, about 100 to about 120 mg. In some embodiments, the amount of S-oxprenolol in the composition is about 80 to about 160 mg. In some embodiments, the composition is suitable for oral administration.

In sonic embodiments, the composition useful for treating muscle weakness is provided in a slow release form. For example, oxprenolol can be administered in slow release form. (Eur J Drug Metab Pharmacokinet. 1998 Apr-Jun; 23(2):178-84; Bennett P N, Bennett J, Bradbrook I, Francis J, John V A, Rogers H, Turner P, Warrington S J. Br J Clin Pharmacol. 1985; 19 Suppl. 2:1715-1755; and Woods K L, Jack D B, Kendall M J, Halsey A, O'Donnell M L, Warrington S J, John V A. Br J Clin Pharmacol. 1985; 19 Suppl 2:177S-184S.)

Also provided are articles of manufacture comprising the compositions, formulations, and unit dosages described herein in suitable packaging for use in the methods of treatment, methods of administration, and dosage regimens described herein. Suitable packaging for compositions described herein are known in the art, and include, for example, vial (such as sealed vials), vessels (such as sealed vessels), ampules, bottles, jars, flexible packaging (e.g., sealed Mylar or plastic bags), and the like. These articles of manufacture may further be sterilized and/or sealed.

Dosages and Administration Route

The dosage of the compositions described herein administered to an individual (such as a human) may vary with the particular composition, the method of administration, and the particular stage of muscle weakness. The amount should be sufficient to produce a desirable response, such as a therapeutic or prophylactic response against muscle weakness. In some embodiments, the amount of the composition is a therapeutically effective amount. In some embodiments, that amount of the composition is a prophylactically effective amount. In some embodiments, the amount of total oxprenolol in the composition is below the level that induces a toxicological effect (i.e., an effect above a clinically acceptable level of toxicity) or is at a level where a potential side effect can be controlled or tolerated when the composition is administered to the individual.

In some embodiments, the amount of an S-enantiomerically enriched composition of a beta blocker or a pharmaceutically acceptable salt thereof (e.g., S-oxprenolol) in the composition is included in any of the following ranges: about 0.5 to about 5 mg, about 5 to about 10 mg, about 10 to about 15 mg, about 15 to about 20 mg, about 20 to about 25 mg, about 20 to about 50 mg, about 25 to about 50 mg, about 50 to about 75 mg, about 50 to about 100 mg, about 75 to about 100 mg, about 100 to about 125 mg, about 125 to about 150 mg, about 150 to about 1.75 mg, about 175 to about 200 mg. In some embodiments, the amount of an S-enantiomerically enriched composition of a beta blocker or a pharmaceutically acceptable salt thereof (e.g., S-oxprenolol) in the composition is included in any of the following ranges: about 5 to about 10 mg, about 10 to about 20 mg, about 20 to about 30 mg, about 30 to about 40 mg, about 40 to about 50 mg, about 50 to about 60 mg, about 60 to about 70 mg, about 70 to about 80 mg, about 80 to about 90 mg, about 90 to about 100 mg, about 100 to about 110 mg, about 110 to about 120 mg, about 120 to about 130 mg, about 130 to about 140 mg, about 140 to about 150 mg, about 150 to about 160 mg. In some embodiments, the amount of an S-enantiomerically enriched composition of a beta blocker or a pharmaceutically acceptable salt thereof (e.g., S-oxprenolol) in the composition is about 20 to about 160 mg, including for example about 50 to about 150 mg, 80 to about 150 mg, about 90 to about 140 mg, about 100 to about 120 mg. In some embodiments, the amount of an S-enantiomerically enriched composition of a beta blocker or a pharmaceutically acceptable salt thereof (e.g., S-oxprenolol) in the composition is about 80 to about 160 mg.

In some embodiments, the amount of an S-enantiomerically enriched composition of a beta blocker or a pharmaceutically acceptable salt thereof (e.g., S-oxprenolol) in the composition includes at least about any of 0.1 mg/kg, 0.5 mg/kg, 1 mg/kg, 2.5 mg/kg, 5 mg/kg, 7.5 mg/kg, 10 mg/kg, 15 mg/kg, or 20 mg/kg. In some embodiments, the amount of an S-enantiomerically enriched composition of a beta blocker or a pharmaceutically acceptable salt thereof (e.g., S-oxprenolol) in the composition includes less than about any of 35 mg/kg, 30 mg/kg, 25 mg/kg, 20 mg/kg, 15 mg/kg, 10 mg/kg, 5 mg/kg, 2.5 mg/kg, 2 mg/kg, 1 mg/kg, 0.5 mg/kg, or 0.1 mg/kg.

Exemplary dosing frequencies include, but are not limited to, daily without break; weekly without break; weekly, three out of four weeks; once every three weeks; once every two weeks; weekly, two out of three weeks. In some embodiments, the composition is administered about once every 2 weeks, once every 3 weeks, once every 4 weeks, once every 6 weeks, or once every 8 weeks. In some embodiments, the composition is administered at least about any of 1×, 2×, 3×, 4×, 5×, 6×, or 7× (i.e., daily) a week. In some embodiments, the intervals between each administration are less than about any of 6 months, 3 months, 1 month, 20 days, 15, days, 12 days, 10 days, 9 days, 8 days, 7 days, 6 days, 5 days, 4 days, 3 days, 2 days, or 1 day. In some embodiments, the intervals between each administration are more than about any of 1 month, 2 months, 3 months, 4 months, 5 months, 6 months, 8 months, or 12 months. In some embodiments, there is no break in the dosing schedule. In some embodiments, the interval between each administration is no more than about a week. In some embodiments, the composition is administered daily. In some embodiments, the composition is administered twice daily. In some embodiments, the composition is administered at least once (such as at least any of 2×, 3×, or 4×) daily.

The administration of the composition can be extended over an extended period of time, such as from about a month up to about seven years or life-long. In some embodiments, the composition is administered over a period of at least about any of 2, 3, 4, 5, 6, 7, 8, 9, 10, 11, 12, 18, 24, 30, 36, 48, 60, 72, or 84 months or life-long. In some embodiments, the composition is administered over a period of at least one month, wherein the interval between each administration is no more than about a week.

The compositions described herein can be administered to an individual (such as human) via various routes, including, for example, intravenous, intra-arterial, intraperitoneal, intraportal, intrapulmonary, oral, inhalation, intravesicular, intramuscular, intra-tracheal, subcutaneous, intraocular, intrathecal, transmucosal, and transdermal. In some embodiments, sustained continuous release formulation of the composition may be used.

Once improvement of the patient's condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms. Patients may also require chronic treatment on a long-term basis.

Pharmaceutical Formulations and Administration

The pharmaceutical compositions described herein may be formulated as solutions, emulsions, suspensions, dispersions, or inclusion complexes such as cyclodextrins in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms. Pharmaceutical compositions of the embodiments may be administered by a suitable route of delivery, such as oral, parenteral, rectal, nasal, topical, or ocular routes, or by inhalation. Preferably, the compositions are formulated for intravenous or oral administration.

For oral administration, the compositions may be provided in a solid form, such as a tablet or capsule, or as a solution, emulsion, or suspension. Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid, or talc. If desired, the tablets may be coated with a material such as glyceryl monostearate or glyceryl distearate to delay absorption in the gastrointestinal tract, or may be coated with an enteric coating. The oral formulations may be presented as discrete units such as capsules, cachets or tablets, each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil such as peanut oil or olive oil, liquid paraffin, a mixture of mono and di-glycerides of short chain fatty acids, polyethylene glycol 400, or propylene glycol.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose), surface-active or dispersing agent. Moulded tablets may he made by moulding in a suitable machine a mixture of the powdered compound moistened with an inert liquid diluent. The tablets may optionally he coated or scored and may be formulated so as to provide slow or controlled release of the active ingredient therein using, for example, hydroxypropylmethylcellulose in varying proportions to provide desired release profile.

Liquids for oral administration may be in the form of suspensions, solutions, emulsions, or syrups, or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

For parenteral use, including intravenous, intramuscular, intraperitoneal, intranasal, or subcutaneous routes, the compositions may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampoules or disposable injection devices, in multi-dose forms such as vials from which the appropriate dose may be withdrawn, or in a solid form or pre-concentrate that can be used to prepare an injectable formulation. Formulations suitable for parenteral including intravenous administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily sub-dose or an appropriate fraction thereof, of an active ingredient.

Drug Combinations

The methods of the embodiments comprise administering an effective amount of at least one compound of the embodiments; optionally the compound may be administered in combination with one or more additional therapeutic agents, particularly therapeutic agents known to be useful for treating muscle weakness afflicting a subject.

The additional active ingredients may be administered in a separate pharmaceutical composition from a compound of the embodiments or may he included with a compound of the embodiments in a single pharmaceutical composition. The additional active ingredients may be administered simultaneously with, prior to, or after administration of a compound of the embodiments.

In certain embodiments, the additional therapeutic agent is selected from the group consisting of anabolic steroids, testosterone, nandrolone, oxandrolone, megestrol acetate, ghrelin agonists, selective androgen receptor modulators (SARMs), amino acid or other nutritional supplements.

Kits

The present application also provides kits, medicines, compositions, and unit dosage forms for use in any of the methods described herein.

Kits provided herein include one or more containers comprising any one of the compositions described herein and/or other agent(s), and in some embodiments, further comprise instructions for use in accordance with any of the methods described herein. The kit may further comprise a description of selection of individual suitable for treatment. Instructions supplied in the kits of the invention are typically written instructions on a label or package insert (e.g., a paper sheet included in the kit), but machine-readable instructions (e.g., instructions carried on a magnetic or optical storage disk) are also acceptable.

For example, in some embodiments, the kit comprises a) an S-enantiomerically enriched composition of a beta blocker or a pharmaceutically acceptable salt thereof (e.g., S-oxprenolol) and a pharmaceutically acceptable carrier and b) instructions for administering the composition for treatment of muscle weakness. The present disclosure provides, in some embodiments, a kit comprising a pharmaceutical composition comprising oxprenolol or a pharmaceutically acceptable salt thereof and a pharmaceutically acceptable carrier, wherein the composition is enantiomerically enriched for S-oxprenolol, and instruction for using the pharmaceutical composition for treating muscle weakness.

The kits of the invention are in suitable packaging. Suitable packaging include, but is not limited to, vials, bottles, jars, flexible packaging (e.g., sealed Mylar or plastic bags), and the like. Kits may optionally provide additional components such as buffers and interpretative information. The present application thus also provides articles of manufacture, which include vials (such as sealed vials), bottles, jars, flexible packaging, and the like.

The instructions relating to the use of the compositions generally include information as to dosage, dosing schedule, and route of administration for the intended treatment. The containers may be unit doses, bulk packages (e.g., multi-dose packages) or sub-unit doses. For example, kits may be provided that contain sufficient dosages of S-oxprenolol as disclosed herein to provide effective treatment of an individual for an extended period, such as any of a day, a week, 8 days, 9 days, 10 days, 11 days, 12 days, 13 days, 2 weeks, 3 weeks, 4 weeks, 6 weeks, 8 weeks, 3 months, 4 months, 5 months, 7 months, 8 months, 9 months, or more. Kits may also include multiple unit doses of the pharmaceutical compositions and instructions for use and packaged in quantities sufficient for storage and use in pharmacies, for example, hospital pharmacies and compounding pharmacies.

Also provided are medicines, compositions, and unit dosage forms useful for the methods described herein. For example, the present disclosure provides, in some embodiments, an S-enantiomerically enriched composition of a beta blocker or a pharmaceutically acceptable salt thereof (e.g., 5-oxprenolol) for treating muscle weakness in an individual. The present disclosure also provides, in some embodiments, an S-enantiomerically enriched composition of a beta blocker or a pharmaceutically acceptable salt thereof (e.g., S-oxprenolol) for preventing body weight loss in an individual with muscle weakness; preventing and treating muscle wasting in an individual with muscle weakness; or improving quality of life in an individual with muscle weakness.

For example, the present disclosure provides, in some embodiments, a pharmaceutical composition comprising oxprenolol or a pharmaceutically acceptable salt thereof and a pharmaceutically acceptable carrier, wherein the composition is enantiomerically enriched for S-oxprenolol for use in treating muscle weakness.

For example, the present disclosure provides, in some embodiments, an S-enantiomerically enriched composition of a beta blocker or a pharmaceutically acceptable salt thereof (e.g., S-oxprenolol) for the manufacture of a medicament for treating muscle weakness in an individual. The present disclosure also provides, in some embodiments, an S-enantiomerically enriched composition of a beta blocker or a pharmaceutically acceptable salt thereof (e.g., S-oxprenolol) for the manufacture of a medicament for preventing body weight loss in an individual with muscle weakness; preventing and treating muscle wasting in an individual with muscle weakness; or improving quality of life in an individual with muscle weakness.

Those skilled in the art will recognize that several embodiments are possible within the scope and spirit of this invention. The invention will now be described in greater detail by reference to the following non-limiting examples. The following examples further illustrate the invention but, of course, should not be construed as in any way limiting its scope.

EXAMPLES

Example 1

The effect of a disclosed composition can be evaluated in patients suffering from one or more of the causes of acute muscle weakness disclosed herein by comparing patients treated to their pre-treatment strength or to patients not so treated. Muscle weakness improvement can be assessed by asking the patient their opinion of muscle strength and/or by measuring one or more of the tests of muscle strength mentioned above. The tests can include measuring muscle strength by hand grip strength, leg extension force, weight lifting, stair climbing power, short physical performance battery (SPPB) test, 6 minute corridor walk test distance, shuttle test speed or other tests of muscle strength, force, fatiguability or power. The tests can also evaluate muscle bulk, by measurement by CT scan, MRI or bioimpedance. The patients can be compared after treatment to before treatment or can be compared to other patients not so treated. The trial may be designed as a parallel group or cross-over design. Muscle improvement can be shown either by reducing the rate of muscle getting weaker or more wasted or by the muscle getting stronger or having an increase in mass and/or bulk.

The invention claimed is:

1. A method of treating acute muscle weakness caused by musculoskeletal injury in an individual in need of said treatment, the method comprising administering to the individual an effective amount of an S-enantiomerically enriched composition of pindolol or a pharmaceutically acceptable salt thereof.

2. The method of claim 1, wherein the muscle weakness is localized.

3. The method of claim 1, wherein the individual has undergone surgery.

4. The method of claim 3, wherein the surgery is abdominal, orthopedic, cardiac, brain, lung, eye, or head and neck surgery.

5. The method of claim 1, wherein the individual has been immobilized.

6. The method of claim 1, wherein the individual has been immobilized for at least 48 hours.

7. The method of claim 1, wherein the individual has suffered a major trauma.

8. The method of claim 7, wherein the trauma affects large bones, abdominal organs, chest organs, or the head.

9. The method of claim 1, wherein the individual has suffered fractures of the long bones of the arm or leg.

10. The method of claim 1, wherein the composition comprises an enantiomeric excess of at least about 50% of S-pindolol or a pharmaceutically acceptable salt thereof.

11. The method of claim 10, wherein the composition comprises an enantiomeric excess of at least about 80% of S-pindolol or a pharmaceutically acceptable salt thereof.

12. The method of claim 11, wherein the composition comprises an enantiomeric excess of at least about 99% of S-pindolol or a pharmaceutically acceptable salt thereof.

13. The method of claim 12, wherein the composition comprises an enantiomeric excess of at least about 99.9% of S-pindolol or a pharmaceutically acceptable salt thereof.

14. The method of claim 1, wherein the composition is administered orally or intravenously.

15. The method of claim 1, wherein the amount of S-pindolol or a pharmaceutically acceptable salt thereof in the composition is about 80 to about 160 mg daily.

16. The method of claim 1, wherein the composition is administered daily or twice daily.

* * * * *